United States Patent [19]

Kroy et al.

[11] Patent Number: 5,252,294
[45] Date of Patent: Oct. 12, 1993

[54] MICROMECHANICAL STRUCTURE

[75] Inventors: Walter Kroy, Ottobrunn; Helmut Seidel, Starnberg; Eduard Dette, Vagen; Max Koniger, Munich; Peter Deimel, Langenpreising; Florian Binder, Traunstein; Reinhold Hilpert, Munich, all of Fed. Rep. of Germany

[73] Assignee: Messerschmitt-Bölkow-Blohm GmbH, Munich, Fed. Rep. of Germany

[21] Appl. No.: 830,755

[22] Filed: Feb. 3, 1992

Related U.S. Application Data

[63] Continuation of Ser. No. 359,713, May 31, 1989.

[30] Foreign Application Priority Data

Jun. 1, 1988 [DE] Fed. Rep. of Germany ....... 3818614
Jul. 29, 1988 [JP] Japan ................... 3825907

[51] Int. Cl.$^5$ .................. G01N 21/00; C12M 1/00
[52] U.S. Cl. .................. 422/102; 422/68.1; 422/82.11; 422/63; 435/287; 435/300
[58] Field of Search ............. 422/58, 102, 82.11, 422/68.1, 63; 437/901, 902, 921; 357/25, 55; 148/DIG. 12; 435/300, 287; 156/662, 663, 647

[56] References Cited

U.S. PATENT DOCUMENTS

| | | | |
|---|---|---|---|
| 3,973,320 | 8/1976 | Greco et al. | 437/902 |
| 4,233,029 | 11/1980 | Columbus | 422/68.1 |
| 4,740,410 | 4/1988 | Muller et al. | 428/133 |
| 4,778,989 | 10/1988 | Hagemayer et al. | 250/227 |
| 4,874,500 | 10/1989 | Madou et al. | 357/25 |
| 4,895,615 | 1/1990 | Muschke | 156/662 |

FOREIGN PATENT DOCUMENTS

| | | |
|---|---|---|
| 0250948 | 6/1987 | European Pat. Off. |
| 3613181 | 10/1987 | Fed. Rep. of Germany |
| 3634573 | 10/1987 | Fed. Rep. of Germany |
| 3602796 | 1/1988 | Fed. Rep. of Germany |
| 3619778 | 1/1988 | Fed. Rep. of Germany |
| 3701295 | 9/1988 | Fed. Rep. of Germany |
| 3715674 | 12/1988 | Fed. Rep. of Germany |
| 3804200 | 8/1989 | Fed. Rep. of Germany |
| 3804751 | 8/1989 | Fed. Rep. of Germany |
| 3811052 | 8/1989 | Fed. Rep. of Germany |
| 3817153 | 11/1989 | Fed. Rep. of Germany |

OTHER PUBLICATIONS

Angell et al., "Silicon Micromechanical Devices", Apr. 1983, pp. 44-55.
Laser and Optoelectronik, No. 4, 1986, pp. 323-336.
W. A. Little, AIP Proceedings for Future Trends in Superconductive Electronics, p. 421, 1978.

Primary Examiner—Robert J. Warden
Assistant Examiner—T. A. Trembley
Attorney, Agent, or Firm—Kenyon & Kenyon

[57] ABSTRACT

A micromechanical structure with cavities, containers, openings, canals, depressions, humps or the like for examinations of sample substances for possible changes of physical and/or chemical properties with targeted evaluation and documentation for the purposes of biotechnology, gene technology, cell and immune research and other medical, agricultural and environment research, where the structure consists of semiconducting material (of the group III to V of the elements of the periodic system) or contain the latter or glass or ceramic, diamond, or carbon and is made by a masking technique, especially by a chemical etching technique.

15 Claims, 6 Drawing Sheets

MICROMECHANICAL STRUCTURE

This is a continuation, of application Ser. No. 359,713, filed May 31, 1989, entitled Micromechanical Structure.

BACKGROUND OF THE INVENTION

The present invention relates to a micromechanical structure for purposes of biotechnology, gene technology, cell research, pharmacology for healing and research on sicknesses which have been uncurable to date, also for agriculture research, to open up new sources of nutrition and energy and to restore the environment, for purposes of medicine, for instance, blood analysis but also of tissue and cells, for instance, antibody, antigen immobilization for preparing monoclonal antibodies, for preparing antibiotics, insulin and also for medications, sera, bacterial and other substance investigations and comparison tests. There is always the problem of safely controlled handling of the respective substance during and after an investigation, reaction or the like, especially if the substances can constitute a danger for the environment.

To meet the purposes mentioned above, particularly for fighting sickness and hunger in the world, it is necessary to be able to safely handle, in investigations, reactions, tests, comparison investigation and investigation series with, in particular, dangerous substances, also if the amounts of substance are ever so small.

SUMMARY OF THE INVENTION

It is an object of the present invention to facilitate or ensure clean, safe storage and handling of substances which are dangerous or could become so, be it prior to, during or after an investigation, reaction, test or the like The above and other objects of the invention are achieved by a micromechanical structure with cavities, for investigating sample substances for possible changes of physical and/or chemical properties and/or biochemical properties, evaluation and documentation in a targeted manner for the purposes of biotechnology, gene technology, cell and immunity research and other medical, agricultural and environment research, wherein the structure comprises at least one of the group of semiconductive material (of the group III to V of the elements of the periodic system), glass, ceramic, diamond or carbon and is made by a masking technique, particularly by chemical etching techniques.

This microstructure has many advantages. It can be produced cost-effectively in large quantities. It is suitable for the safe storage for a multiplicity of substances such as samples for tests, for treatments, for investigation, for comparisons, for reactions, etc. The arrangement of suitable cavities relative to each other in the structure in the manner of a matrix or an array permits simple process control and the carrying-out of desired reactions, of desired small amounts of substance as well as their targeted treatment and examination. The structure with the cavities consists of inert material, i.e., it does not change in the investigations and treatments; the cavities can be closed off reliably and are not attacked by most toxic substances.

BRIEF DESCRIPTION OF THE DRAWINGS

The invention will be described in greater detail in the following detailed description with reference to the drawings, in which.

DETAILED DESCRIPTION

Figure 1:
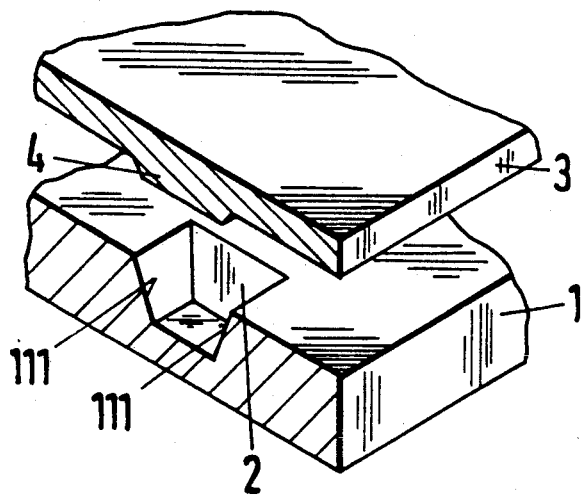
FIG. 1 shows a structure with a single cavity and a definite surface orientation of the crystalline material.

As shown in FIG. 1, a structure 1 consists of walls with one and preferably several cavities therein to contain small amounts of substance, and the block is closed off with a cover 3. The block 1 and the cover 3 are made of crystalline material such as semiconductor material. Likewise, for closing off the container according to the invention, a counterpiece, cover 3, is generated with a second mask which has humps 4 corresponding to the depressions 2, since the masks are geometrically identical. The mask technique permits high precision in production; it is known per se from semiconductor technology.

With the mentioned technique it is an advantage to apply an anisotropic etching method depending on the crystal orientation because thereby, utilizing the self-limiting action of (111) crystal planes, depressions with high geometric precision and very narrow tolerances can be realized. The container in FIG. 1 can be produced on (100) silicon, where the laterally limiting (111) planes make an angle of 54.7° to the wafer surface The invention is not limited to the abovementioned etching technique. Other known kinds of making depressions in semiconductor or similar crystalline materials can be applied such as laser beam drilling.

Figure 5:
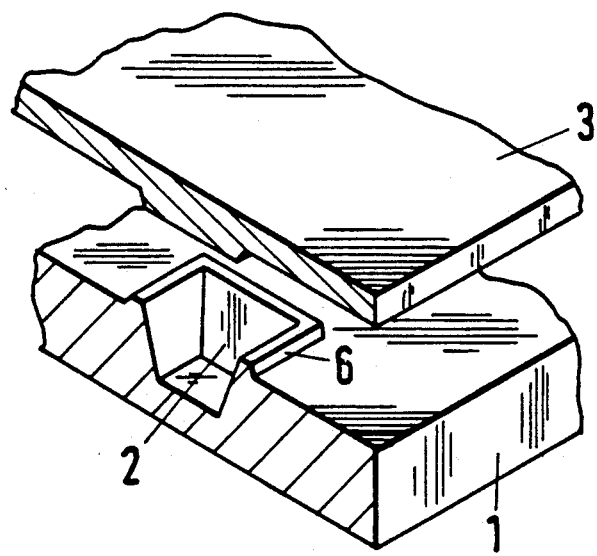
FIG. 5 shows a structure in a design modification of FIG. 1.

The cover 3 can be provided with a hump 4 which has the same 54.7° inclination to the crystal surface as the container block 1 in the area 2 and therefore seals perfectly tight. This is true also if the cover has a multiplicity of humps and the block 1 a multiplicity of depressions 2. If the fitting accuracy of the humps and depressions at the cover 3 and the block 1, made by the etching method are not sufficient for specific applications of particularly dangerous substances, a circular seal can be used in addition. FIG. 5 shows an embodiment which in turn corresponds to the 54.7° inclination of the hump form of the cover and form a closure with a further inclination. In addition, adhesives or other joining techniques can be used for increasing the tightness. In particular, a laser beam can also be used with a seam welding process at the circular rim of the cover. A multiplicity of cavities 2 is not limited as far as size, design and distribution in the block of the container.

Figure 2:
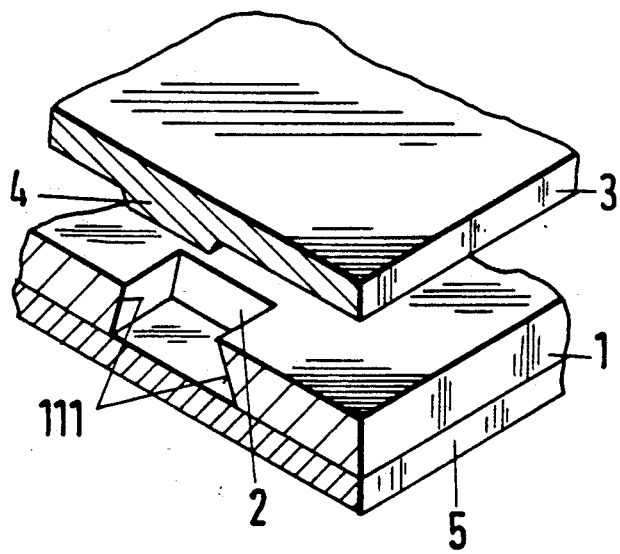
FIG. 2 shows a modification of FIG. 1.
Figure 4:
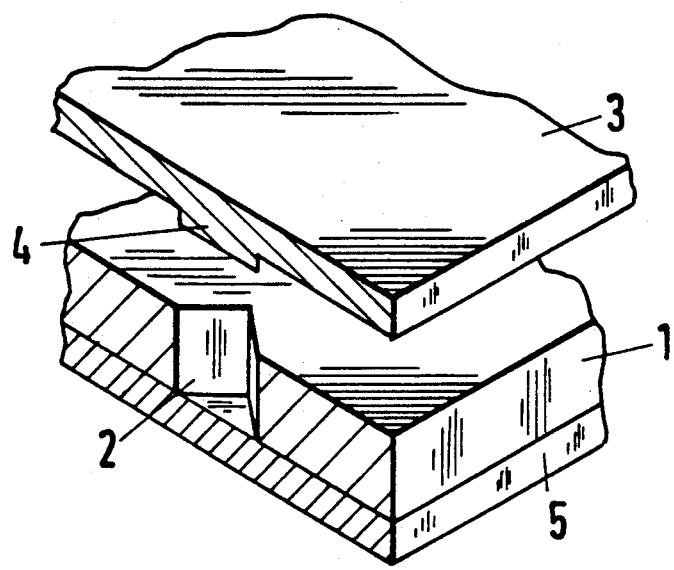
FIG. 4 shows a structure as a modification of FIG. 3.

The cavities 2 (and the humps 4) may, in particular, be square, rectangular, circular, oval or diamond-shaped. They can be tapered or expanded toward the body, see FIG. 1 and FIG. 2, or keep the same cross section if drilled, for instance, with a laser beam (FIG. 4). They can have also other cross sections or shapes (openings, canals).

An additional layer or plate 5 serves as a carrier or intermediate carrier (removable) advantageously of the same material, for instance, silicon or the like, as the body of the container, likewise providing a hermetically tight closure.

The structure 1 worked out from a block material advantageously (for mass production) forms a plane plate with through cavities 2 such as openings, canals or the like of desired shape etched by wet chemistry, advantageously from silicon, while the cover 3 and the bottom 5 consist of material which can be joined preferably well to this material of the structure 1, especially of material which can be sealed off hermetically tight such as glass, silica, glass ceramic or synthetic silicon or silicon metal compound material.

Figure 3:
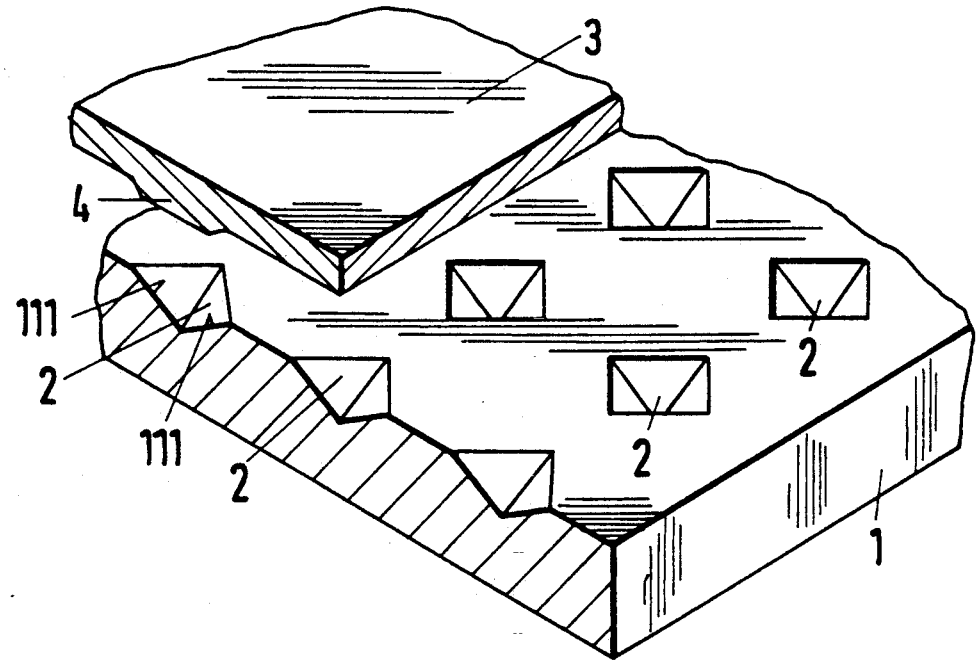
FIG. 3 shows a structure of crystalline material.
Figure 6:
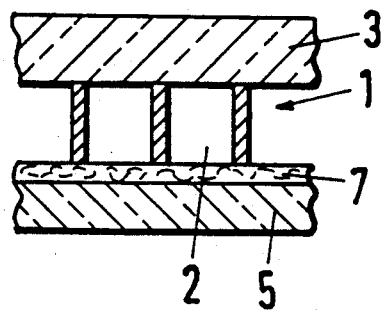
FIG. 6 shows a modification of FIG. 2 or 4, where a structured portion in the center between portions different therefrom is arranged (sandwich construction)

In FIG. 6, the bottom 5 is further covered, as shown in FIG. 6, with a layer 7 which may be, for instance, a filter layer, a sedimentation layer, an inert or catalytic or otherwise reacting layer of a material or only absorbing material. A fiber fleece or a woven fleece with large pores and a large open surface, a fiber layout, foam material or a similar permeable structure can be used, depending on the application (collecting, storing, reacting). This may involve a neutral carrier material or an active carrier material which is used for the layer 7 and underneath valves for further devices (see FIG. 8) can be used for the layer 7. The block 1 with the cavities 2 contains them advantageously according to a raster measure in an X-Y distribution over the surface of the preferred silicon crystal as an array or in matrix form (see FIG. 3) so that they can be filled, gassed, injected, thinned, depleted, suctioned off or the like, for instance, by means of automatic devices, mixed or brought to reaction. The supply or discharge organs are then program-controlled line by line until the entire surface is scanned, as known per se, in automatic analyzers or automatic handling devices or robots for medical or other research purposes.

The material of block 1 must in any case be inert against the substance which is to be examined, treated, thinned or mixed. Or is to be the subject of a reaction or is to be tested for a particular result or the lack thereof.

Figure 7:
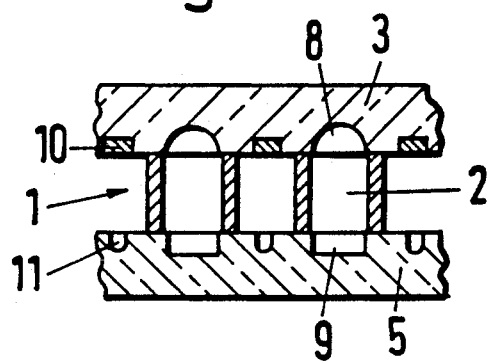
FIG. 7 shows a modification of FIG. 6 with devices additionally arranged in the bottom plate and cover plate.

Depending on the purpose for which the invention is applied, the cavities for examining or storing (storage containers) can be made larger especially if the cavities 2 in block 1 are only part of sampling or examination or reaction chambers-see FIG. 7. The matrix or array arrangement in the X-Y direction is retained as described above and also the essentially sandwich-like construction according to FIG. 6. In addition, there is correlated in the cover plate 3 and the bottom plate 5, with the respective cavity, a further fitting depression 8 or 9 which substantially increases overall the chamber volume or the volume of cavity 2. Then the supply and removal of a medium can then take place also in the plane of the drawing if, for instance, the same medium is to be supplied to or removed from all chambers.

Figure 8:
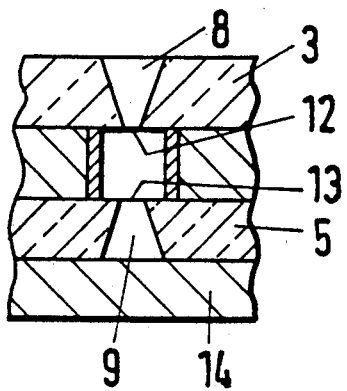
FIG. 8 shows a further modification of FIG. 6 or 7 with additional layers or plates.

As a rule, substances like solids in a fluid are examined for the purposes mentioned at the outset; gases in a liquid or gases or liquid in a solid can be examined. This is true especially for immune reactions, for the examination of enzymes or microorganisms. In examinations or analyses of substance/mixtures, chemical or physical properties or their changes can be ascertained with respect to one or more properties like flow, density, surface or limit effects, especially features or particles, permeability, friction and adhesion. In the simplest case, storage under certain conditions such as pressure or vacuum can be examined over a definite time or a reaction or a failure of a reaction to arrive. External influences can be: radiation, heat treatment, application of reagents, the measurement of the change of material properties under heat, cold, steam, moisture or materials/particles supplied, through the application of electrical/electrochemical or magnetic means, through the application of sound, infrasound, ultrasound. In addition, calorimetric, spectrophotometric or fluorometric investigations, for instance, using reagent layers such as litmus paper can be carried out as layer 7. Heating and/or cooling elements can be taken to the chambers in the form of specifically annealed media in canals 10 and 11, for instance, through the plates 3 and 5 or thermocouples, particularly Peltier elements can be arranged at least partially in the vicinity of these cavities. Substances can be provided with fluorescent markings, with radioactive markings or with enzyme markings with carriers or without carriers, bound or separable, organic or inorganic, with cells or cell fragments, gels or others can be used for detecting microorganisms, bacteria, viruses and others but also for detecting cancer, for determining individual substances in the blood or for determining the pH values, of blood sugar, of blood cholesterol or for detecting narcotics or others in the blood. Suitable methods of analysis particularly biological/medical, chemical/physical ones are known, especially for blood analysis, for the analysis of sera, etc. Also examination methods or other body liquids such as lymph liquid, urine, etc. are known, depending on whether small particles, marked or unmarked, organic/inorganic, with or without carriers of known type are used. Irradiation by means of X-rays but also examinations by means of gamma rays, with visible infrared light or ultraviolet light (optical methods) are recommended. Evaluating methods by means of light guides are shown as examples in FIGS. 9 and 10. In the investigation of the flow properties of substances or mixtures of substances, it is advantageous to control, as is shown in FIG. 8, the inflow, outflow or both (throughput) by means of microvalves 12 and 13 in the cover or bottom 5 of block 1 with the micro properties 2. The micro valves themselves are known per so (see, for instance, European Patent 0 250 948 A2). They are preferably arranged in the same array or in the same matrix in the X-Y direction as the cavities 2 in the block 1 and thereby yield a simple evaluation possibility for respective examinations. A layer 7, as in FIG. 6 can be arranged in the bottom 5. Underneath the bottom 5, a further carrier or termination plate 14 can be arranged which can also comprise a pickup device, for instance, photo cells in the same array arrangement for passing on for evaluation to a micro processor (not shown here). The lines for the supply and discharge of substances, reagents etc. are not shown, neither are the radiation sources which advantageously radiate in FIG. 8 from above, i.e., above the cover 3. Parts 3 and 5 can also consist in FIG. 8 advantageously of glass, silica or silicon ceramic or a composite silicon material and can be at least partially transparent and have at least partially mirror surfaces. The cover or the bottom can be replaced optionally by strips of foil of light-impervious material at least in part; for instance, a plastic foil which brings about a hermetically tight seal but can be pierced by a hollow needle can also be cemented over the cover 3 if the latter contains the micro valves. Foils or layers may be optically transparent or opaque; they can be realized as heating layers 10 or heat sinks 11 or made for optical purposes reflecting-nonreflecting, transparent, as filters, partially transparent or similarly for certain wavelengths. Also carbon or diamond layers and/or mask layers which cover the cavities at times or in part, can be used.

The microvalves can be addressed and driven in a manner known per se or be designed as described in German Patent Application P 38 11 052.0-31. The reaction in the cavities can then take place by movement, for instance, piezoelectrically, magnetically, electrostatically or in similar ways. There, a nutrient solution, a mutant, a reagent or similar substances diluted or enriched can be dosed and the dwelling time can be controlled by respective closing and opening of the microvalve. The heat or cooling treatment can be carried out by means of Peltier elements, heat pipes, Thomson-Joule coolers or similar means.

Silicon sensors are again preferred as sensors, arranged in the same array in the lowermost layer, particularly for the examination of physical or chemical properties such as black/white or gray value, contrast blurring, transmission, transparency, reflection, conductivity, resistivity, capacity, pressure, elongation, temperature volume, quantity, time, etc. For evaluation, the measured values are passed on to a microprocessor or microcomputer, now shown. The readout can be achieved in a manner known per se if the evaluation takes place optically, for instance, in a manner of the above application P 38 17 153.8-33.

Figure 9:
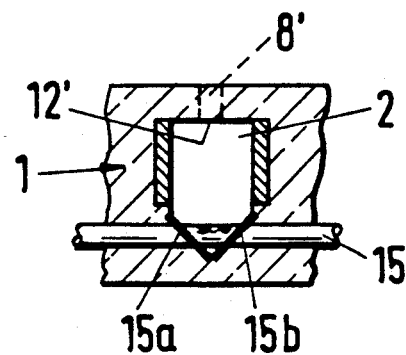
FIG. 9 shows a design with a measuring or pickup device.
Figure 10:
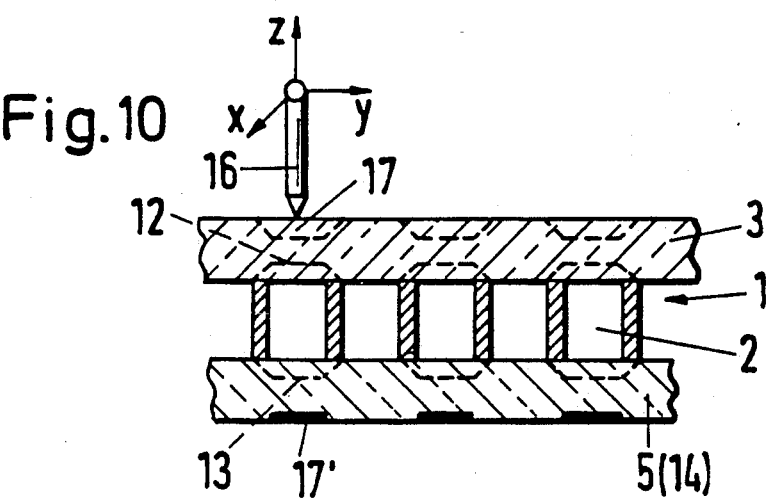
FIG. 10 shows a structure with a measuring and pickup device as well, optionally with memory.

The storage and documentation of the data of the measuring or test program as well as the storage of, for instance, patient data or illness data, or data of sera or pharmaceuticals can take place on the same chip (lowest layer in FIGS. 8 to 10). The storage can be achieved either by means of an optical memory, for instance, according to DE-OS 3 804 751 with amorphous silicon as the storage medium (bubble memory) or as an integrated semiconductor memory (DE-OS 38 17 153) or with a RAM component (P 37 01 295.9-52). As is shown in FIG. 9, it is possible in a simple manner to use in the optical or optoelectronic evaluation, a light waveguide 15 which passes through the micro chamber or cavity 2 in the block 1 or extends to it.

In FIG. 9 the V-moat with its subareas 15a, 15b is changed at a 90° angle for showing subareas, but the light waveguide or optical fiber is longitudinal within the same axis as the V-moat if it passes through the cavity.

Preferably the light waveguide is arranged so that it can distribute light into the cavity to evaluate changes in decoupled light under test-influences, i.e. by measuring transmitted light intensity.

The light can be transmitted between (see FIG. 12) or through the optical fiber or waveguide longitudinally (see FIG. 9) and/or transverse to its axis (i.e. in an arrangement as shown in FIG. 10).

The light waveguide can be used as an information transmitter (bus) for evaluation in a (micro-)processor or (micro-)computer as in German patent 36 19 778.

As can be seen in FIG. 9 too, the mantle of the optical fiber or waveguide is partially destroyed or deterred in a region to get in contact with the substance to be tested or a substrate therefore.

The mantle can be chemically etched off (if of glass) or mechanically peeled off, by a tool (if the mantle is made of plastic).

Modifications of the embodiment according to FIG. 9 are possible in various ways, particularly for the photoelectric or other optoelectric evaluation not only by means of light waveguides. The light waveguides, preferably in V-moats, are arranged fixed resting on their bottoms and not only continuously but also cut off at an angle corresponding to the inclination of the moat. The waveguide arrangement can be made parallel to the moat, transversely to the moat from above or from below at a 90° angle, 180° or similarly. The light waveguides will bring light in and out to the cavity and are connected for test evaluation (of the substance) to photocells such as line sensors or arrays for the purpose of analog or preferably digital readout. The readout can take place in lines and rows, for instance, by means of scanners with the aid of a photoelectric line sensor as described in DE-OS 3 804 200. Transmitters and receivers, especially PIN diodes, can be integrated in the structural unit. The V-angle of the moats are adjustable or variable as to slope (see DE-OS 3 613 181). Integrated optical waveguides and their design and application are described in the journal Laser and Optoelektronik, No. 4, 1986, pages 323 to 336. On page 338 of the same journal, application of light waveguide sensors in medicine are described.

In FIG. 10 is shown a block 1 with bottom 5 and cover 3 and with microcavities 2 especially enlarged by recesses in the cover 3 and bottom 5, similar to FIG. 7, where however, above the microcavity 2 located in the array arrangement, treatment openings, valves, supply and discharge organs, windows, doping zones, etc. according to the chamber volume are disposed in the cover 3, while in the bottom 5, for instance, an array of photoelectric cells or a CCD array or a MOS field effect transistor is arranged which is connected for readout and evaluation, for instance, via the above mentioned optical or an electric bus to an evaluation unit, especially with microprocessors, of the microcomputers. A light pen 16 scans the array line- and columnwise, for instance, in binary code 8×8 microcavities or cells, respectively, or 10×10 for direct digital interrogation. Instead of the light pen 16, a piezoelectric, a capacitive, a magnetic or an electric sensor can find application. The pen 16 is then suitable for applying a voltage, power or light irradiation or something similar, through the windows 17 in the cover 3 into the chambers 2 of the block 1 for direct readout, for instance, via a CCD array in the same arrangement as the microcavities or cells, indicated here by the CCD cells 17'. Similarly, also a MOSFET or a RAM component can be arranged. The readout can also be carried out with components or integrated optics, especially contactless and two-dimensionally (see DE OS 3 605 018 or U.S. Pat. No. 4,778,989). Instead of the light pen 16, an ion-selective measuring electrode can also be used as a replaceable sensor element, particularly for measuring the ion activities in liquids and at textile surfaces. Such ion-selective measuring systems are known and are on the market. They are based on a purely electrical evaluation system in contrast to the embodiment of FIG. 9 which is used, for instance, for the optical determination of the catalytic enzyme activity of a substance sample where the change, due to the enzymic reaction of spectral properties of an enzyme substrate or its reaction products per unit time are picked up. The enzyme substrate is correlated with the exposed region of a light waveguide, with which the sample substance to be measured is brought into contact.

In the embodiment according to FIG. 10, an evaluation by means of a CCD array is advisable, for instance, according to DE-OS 3 817 153 or by means of semiconductors according to DE-OS 3 715 674 or by means of liquid crystal elements such as described, for instance, in German Patent 3,602,796. With such elements, direct storage of a test or analysis result is possible and can be interrogated in targeted fashion at any time, also as to individual microcavities.

Figure 11:
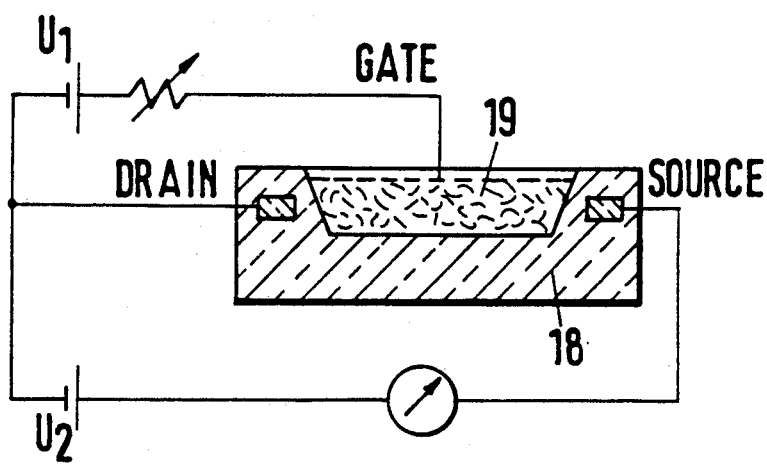
FIG. 11 shows a device with a biosensor, especially a field-effect transistor.
Figure 12:
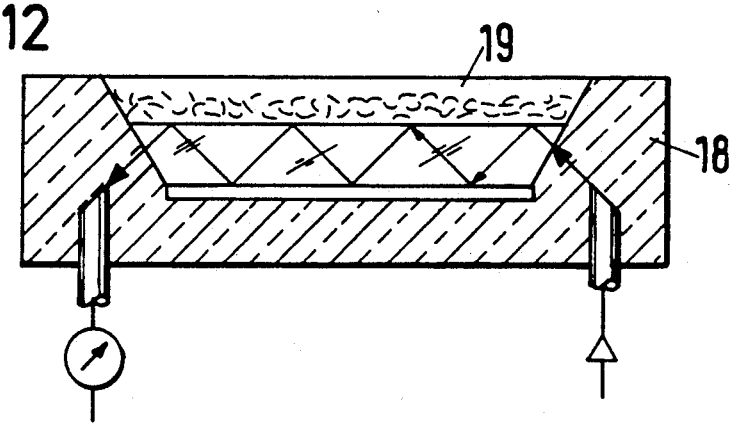
FIG. 12 shows a modification of the embodiment according to FIG. 1.

In FIGS. 11 and 12, optoelectronic/electronic sensors are shown which are adapted to the properties to be examined and are generally known under the term "biosensors". Such biosensors work generally with field-effects transistors 18 in silicon technology. Produced together, the biosensor has here a biological component on the surface which is connected to the gate of a transistor. This biological component or the reaction or enzyme substrate 19 must be able to carry out the respectively desired reaction. Then, after the operating range is optimally adjusted, for instance, at R by means of one or more voltage sources U1, U2, voltage can be applied to a drain and source and corresponding changes in the event of ion activity. The measurement can take place, according to FIG. 12, also photoelectrically, integrated, by means of a light waveguide between the transmitter and receivers such as diodes and lasers A biosensor of the kind under discussion here is described in German Patent 3 634 573.

Figure 13:
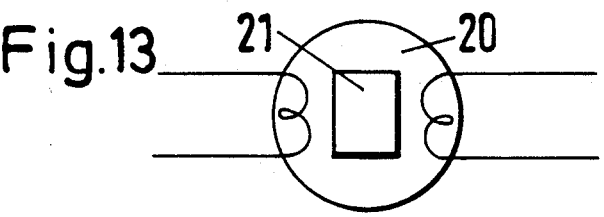
FIG. 13 shows a device for ascertaining given substances in fluids.

In FIG. 13, a sensor on a silicon wafer 20 is shown purely schematically, where a sensor chip 21 is brought to reaction with a substance specimen, for instance, a soil sample, a liquid sample, a food sample or a textile sample with toxic substances contained therein, the percentage of which, for instance, needs to be determined. The required amount of oxygen or the oxygen content or something similar can also be determined. The sensor is a conventional thermistor or a conductivity sensor. Also sound or ultrasound or infrasound sensors are suitable if the sample is to be subjected thereto. Miniature microphones are known for use therewith.

Figure 14:
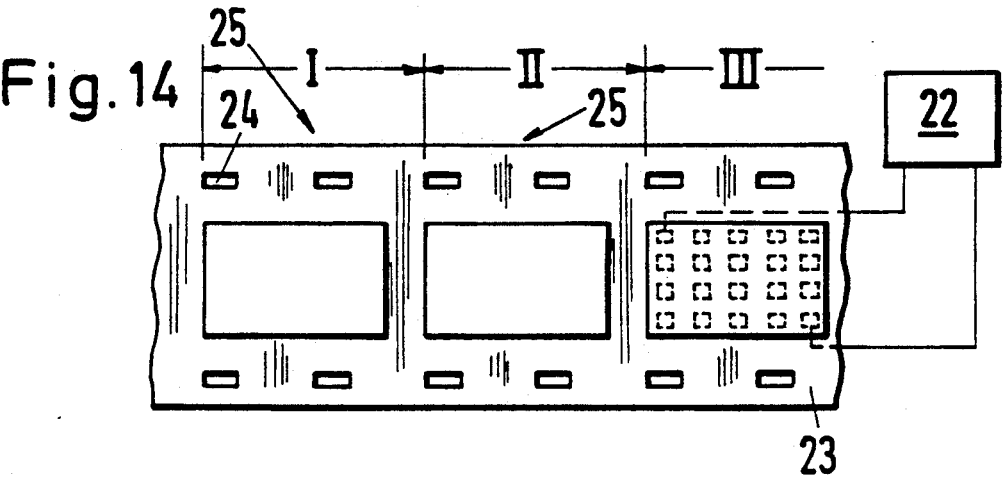
FIG. 14 shows a device for automatic examination with documentation of the examination results.

In FIG. 14, an embodiment of an automatic tester is shown. A microcomputer or microprocessor takes over the control of the test procedure in accordance with a predetermined test program. The program may contain interchangeably external memories, for instance, in a P EPROM or an erasable write-read memory. Patient data of the material to be tested, the reagents, etc. are likewise stored from, upon and after the completion of a test and the test results are likewise stored in the microcomputer or microprocessor, especially in one for freely selectable intervention, and the recording itself is documented, for instance, as a CCD picture, a heat image or on magnetic tape piezoresistively, electrostatically or ferroelectrically, etc.

In the embodiment according to FIG. 14, a film carrier 23 is shown on which macrochips from a multiplicity of individual chips according to FIGS. 1 to 5 are cemented or are fastened detachably, wherein the film carrier has transport perforations 24 in order to conduct the film with the conventional film transports such as a Maltese Cross from roll to roll, is controlled via a treatment time of the program, and from station to station 25, i.e., here I–X. There, one or more substances are first filled, according to a test program, into the microcavities of the chips in station I; in station II, a reaction then takes place either with or without treatment, and at the end of the reaction time measurement takes place automatically and passage into the test station III, so that optionally further tests can be carried out and the test results may be correlated automatically with the individual cavities and optionally with individual sample substances as well as patients. The self-documentation and storage takes place in the microcomputer or microprocessor 22 for the automatic test control and test application.

The invention further provides apparatus for a micromechanical heat exchanger, especially a Joule-Thomson cooler.

According to the present state of the art, there are available on the market various designs of miniaturized heat exchangers such as Joule-Thomson coolers. They are all 8 distinguished by very high unit costs.

A Joule-Thomson cooler available on the market (for instance, from the firm Hymatik) has a very long metal helix which is wound on the surface of a cone. The overall arrangement is contained in a Dewar housing where the expanded gas flows back over a large area via the metal spiral between the Dewar wall and the cone surface provided with cooling fins.

Another arrangement which was published by W. A. Little (AIP Proceedings for Future Trends in Superconductive Electronics, page 421, University of Virginia, Charlottesville, 1978), consists of several glass plates cemented together, into which lateral cooling canals had been worked. These coolers are not very effective since due to the poor thermal conductivity of the glass, the efficiency of the heat exchanger is limited.

The invention attacks the problem of providing a miniaturized heat exchanger, especially a Joule-Thomson cooler which can be manufactured cost-effectively and furnishes increased exchanger performance.

This problem is solved by the provision that in contrast to known designs, the flow canals of a plate heat exchanger are arranged vertically in a thin substrate. This substrate is enclosed (in sandwich fashion) by two cover plates into which connecting canals are worked which close the vertical canals of the substrate as seen in the cross section, to form a meander. The individual cells of the heat exchanger are arranged in spiral shape on the substrate (as seen from above). At the center of the substrate there is an expansion chamber in which the main cooling output is generated. The highly compressed gas meanders from the outside to the inside on the heat exchanger spiral, expands in the second expansion chamber and is then brought to the outside again counterflowwise via canals with substantially expanded cross section, already precooling the inflowing gas. So that the large radial temperature gradient over the substrate can be maintained and to minimize the losses due to heat conduction in the substrate and in the cover plates, vertical separation canals are worked in between the individual arms of the spirals. The overall arrangement is provided at top and bottom with two insulating plates with heat conduction as small as possible (for instance, glass). Glass cover plates can also be connected directly to the central plate (in sandwich fashion).

The invention is suitable in particular for cooling infrared CCDs. As the cooling medium, the highly compressed gas (for instance, nitrogen) is used where the boiling point of the gas can be reached (in the central expansion chamber of the gas) as the limit temperature.

Figure 15:
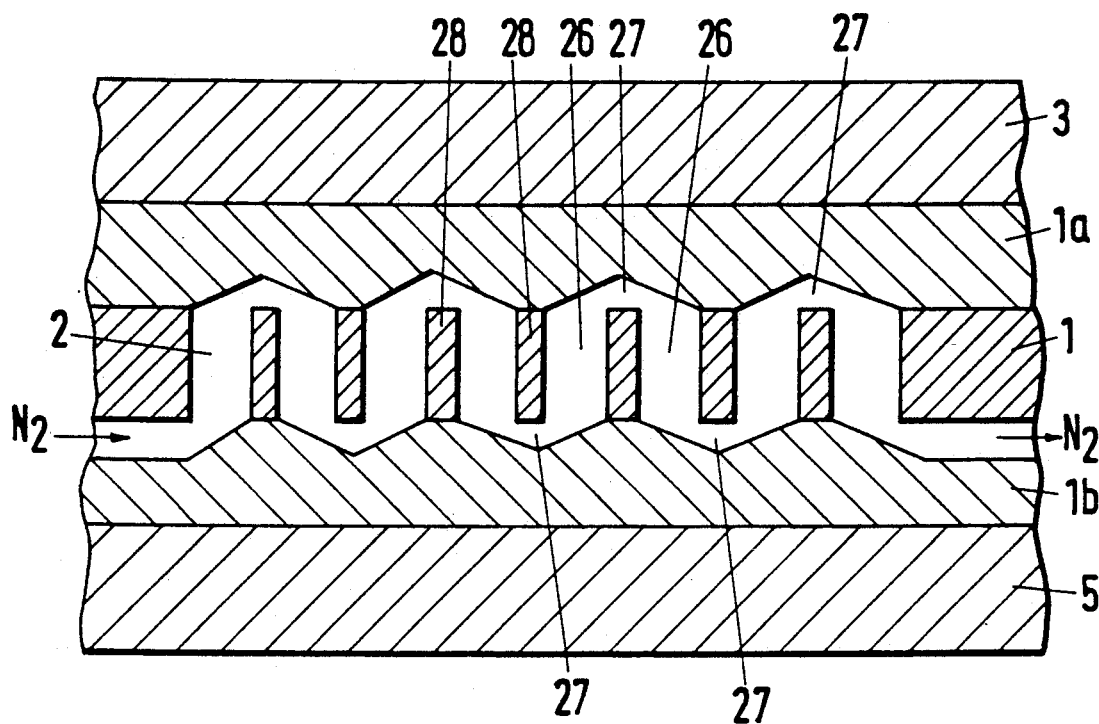
FIG. 15 shows a heat exchanger, especially a plate cooler.
Figure 16:
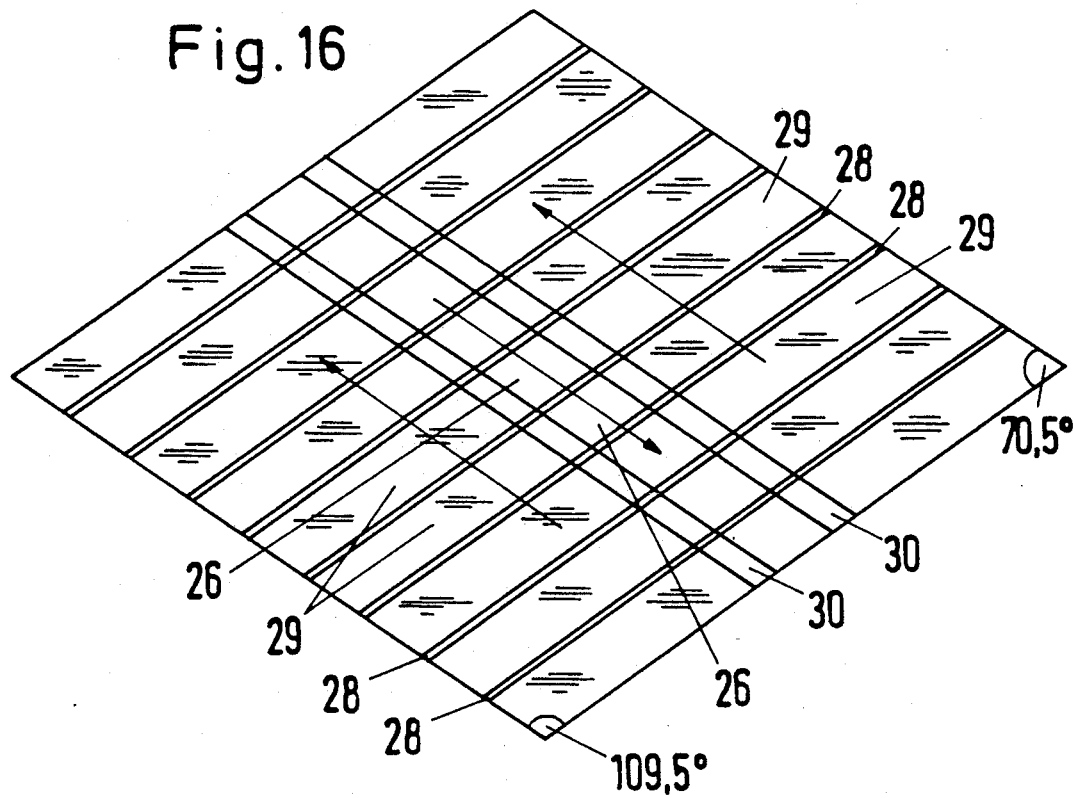
FIG. 16 is a top view of FIG. 15.
Figure 17:
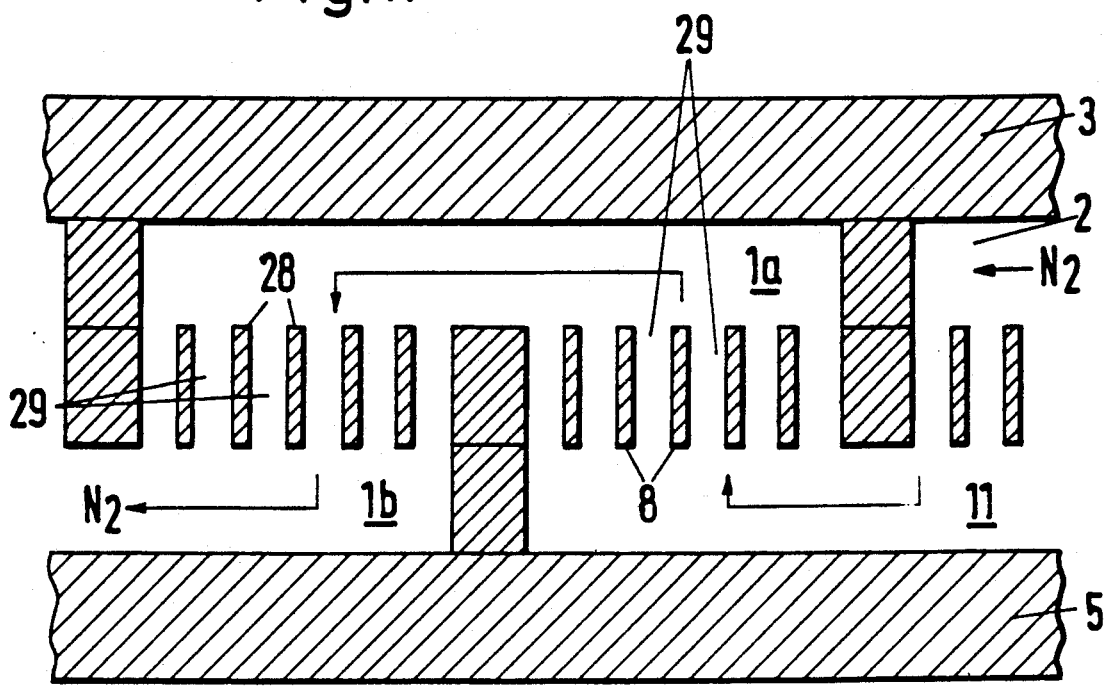
FIG. 17 is modification of FIG. 15.
Figure 18:
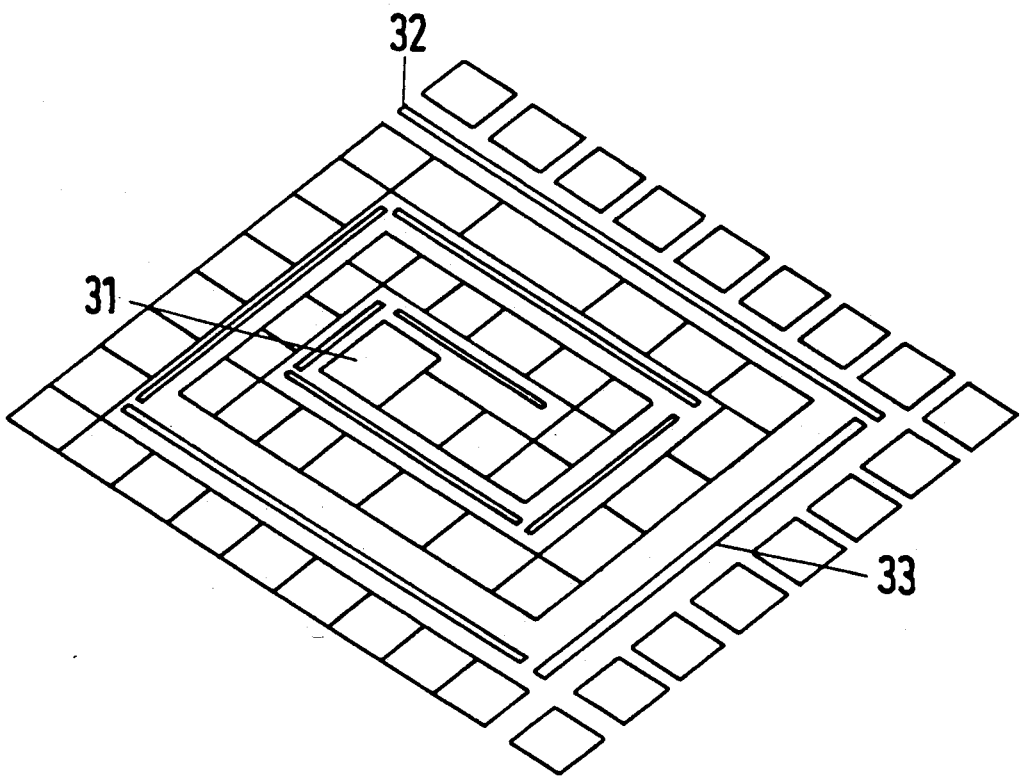
FIG. 18 is top view of FIG. 17.

The invention will be explained in the following, making reference to the embodiment shown in the drawing, where FIG. 15 shows a cross section through a heat exchanger as a Joule-Thomson cooler in the vicinity of the high-pressure canals;

FIG. 16 shows a top view of an elementary heat exchanger cell of the Joule-Thomson cooler in the area of the central silicon disc;

FIG. 17 shows a cross section through the Joule-Thomson cooler in the vicinity of the low-pressure canals, and in FIG. 18 shows an overall arrangement of the elementary heat exchanger cells as well as of the expansion chamber at the center of the silicon disc.

In the following, one embodiment of the Joule-Thomson cooler will be described. The overall arrangement consists of three machined silicon discs 1, 1a, 1b which are connected to each other, and two cover plates, for instance, of glass 3, 5 which in turn are connected to the silicon discs according to FIG. 1.

FIG. 15 shows a cross section of the overall arrangement through the smaller cooling canals 26. Into the upper and lower silicon discs, depressions 27 are etched which close the canals of the central silicon disc to form meanders. These depressions are likewise etched into (110) silicon discs, their depths being limited automatically by the crystallography. The etching is accomplished anisotropically by a batch process.

Into the central silicon disc are worked vertical canals 26 which carry the outflowing and returning gas and at the same time serve as heat exchangers through the thin partitions. One elementary cell of this heat exchanger is shown in FIG. 16. The inner smaller canals 26 carry the compressed outflowing gas (for instance, typically to 50 to 100 bar). The outer large canals 29 are connected to each other so that they form a canal with a large cross section for the returning expanded gas. The partitions in the outer region 28 merely have the purpose to take care of a heat exchange as effective as possible and of mechanical stability. The more strongly designed wall between the high and low pressure canals must take up the entire pressure difference and at the same time make possible a good heat transfer. In this embodiment, the specific geometry of the canals is due to the crystalline structure of silicon, with vertical (111)—planes on (110)—discs.

FIG. 17 shows a cross section through the outer region of the canals 29 for the returning gas. There, the outer silicon discs 1a and 1b are etched through completely in order to obtain a cross section as large as possible for the meanders of the expanded gas.

The overall arrangement of the individual heat exchanger cells on the central silicon disc is shown in FIG. 18. The cells are arranged side by side and are brought in spiral fashion from the outer region into the center of the disc. In the center of the disc there is an expansion chamber 31, in which the cooling output is generated. On top of this chamber a silicon chip or a similar semiconductor or ICs can be arranged, for instance, directly. The individual spiral arms are thermally insulated from each other by separation canals 32, 33.

The novel micromechanical Joule-Thomson cooler is distinguished from the existing systems primarily due to the fact that it can be produced substantially more cheaper by the known batch process methods of micromechanics such as are used in the manufacture of semiconductor components. Furthermore, due to the vertical arrangement of the cooling canals and the frequent meanders, very high turbulence of the gas and therefore high efficiency of the heat exchanger can be expected. Furthermore, a semiconductor chip to be cooled can be integrated directly into the system or overall arrangement so that the cold output is generated directly at the chip without further partitions.

The invention is not limited to the use of a certain medium for the heat exchange. In addition, the conduction of the media is not limited to the embodiment shown. Heat pipes can also be used.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. A micromechanical structure for investigation of sample substances in a targeted manner, comprising a masked-formed, etched structure with a plurality of depressions formed in an array that is made of at least one of a group of semiconductive materials, glass, ceramic, diamond, and carbon, the masked-formed, etched structure including a bottom structure, which has a plurality of depressions formed in an array, and a lid structure, which has a plurality of humps formed in an array, the lid and bottom structures being formed so the plurality of depressions and humps are at corresponding positions and have a same geometry, and so that when the lid structure is combined with the bottom structure, the plurality of corresponding depressions and humps are in alignment and form a plurality of microcontainments for containing one or more sample substances for evaluation and/or documentation of possible changes in one or more properties of the sample substances.

2. The micromechanical structure recited in claim 1, wherein the lid and bottom structures comprise the same material.

3. The micromechanical structure recited in claim 1, wherein the lid and bottom structures comprise silicon or another microcrystalline material or glass.

4. The micromechanical structure recited in claim 1, wherein the plurality of depressions are of defined form, size, arrangement, and distribution, and are in a surface of the bottom structure facing the lid structure.

5. The micromechanical structure recited in claim 4, wherein the lid structure fits hermetically tight on the bottom structure.

6. The micromechanical structure recited in claim 4, wherein the plurality of depressions are arranged in a predetermined spiral pattern.

7. The micromechanical structure recited in claim 4, wherein the lid structure has openings arranged in a same array as the depressions in the bottom structure, with the openings being capable of being closed, and wherein the lid structure further includes measuring and evaluating means for connection to computer means.

8. The micromechanical structure recited in claim 7, wherein the measuring and evaluating means are selected from the group consisting of optical, opto-electronic, electronic, piezoelectric, ferritic, magnetic, capacitive, ohmic or other measuring devices.

9. The micromechanical structure recited in claim 8, wherein the measuring and evaluating means are for individual measurements and evaluations of the individual contents of each of the plurality of depressions.

10. The micromechanical structure recited in claim 4, wherein a light waveguide distributes light into the plurality of depressions through the lid and bottom structures to evaluate changes in decoupled light by measuring transmitted intensity.

11. The micromechanical structure recited in claim 4, wherein the masked-formed, etched structure further comprises a detector for measuring external influences on the content of the individual depressions of the plurality of depressions.

12. The micromechanical structure recited in claim 1, wherein the arrangement of the plurality of depressions is provided in the array in matrix form, so that the matrix can be scanned by automatic filling or discharge and/or mixing and/or diluting/dosing means.

13. The micromechanical structure recited in claim 12, wherein the masked-formed, etched structure further comprises a plurality of microvalves which form a matrix which can be scanned in accordance with a predetermined program, the microvalves being arranged in the same array as the plurality of depressions.

14. The micromechanical structure recited in claim 1, wherein at least one depression of the plurality of depressions comprises a bio-sensor and/or biological-chemical sensor which includes a transistor containing a source and drain with a gate control.

15. The micromechanical structure recited in claim 1, wherein several of the masked-formed, etched structures are fixed onto a film carrier for transporting to a plurality of stations for automatic testing and evaluation.

* * * * *